United States Patent [19]

Schröeder et al.

[11] Patent Number: 5,698,715
[45] Date of Patent: Dec. 16, 1997

[54] PREPARATION OF UNSATURATED CYCLIC ETHERS

[75] Inventors: Jürgen Schröeder, Ludwigshafen; Thomas Fetzer, Speyer; Christopher William Rieker, Mannheim; Klaus Ebel, Lampertheim, all of Germany

[73] Assignee: BASF Aktiengesellschaft, Ludwigshafen, Germany

[21] Appl. No.: 695,630

[22] Filed: Aug. 12, 1996

[30] Foreign Application Priority Data

Aug. 23, 1995 [DE] Germany ............... 195 30 993.6

[51] Int. Cl.⁶ .................. C07D 309/18; C07D 307/28
[52] U.S. Cl. .................. 549/346; 549/347; 549/356; 549/377; 549/430; 549/507; 549/510
[58] Field of Search ................... 549/356, 377, 549/507

[56] References Cited

U.S. PATENT DOCUMENTS

| | | | |
|---|---|---|---|
| 2,993,910 | 7/1961 | Dimroth et al. | 549/507 |
| 3,766,179 | 10/1973 | Snapp | 260/244 |
| 4,025,534 | 5/1977 | Sandhack et al. | 260/343.6 |
| 4,048,245 | 9/1977 | Pollitzer et al. | 502/326 |
| 4,079,097 | 3/1978 | Antos | 502/326 |
| 4,088,671 | 5/1978 | Kobylinski | 260/449.6 |
| 4,136,064 | 1/1979 | Hayes et al. | 502/326 |
| 4,701,434 | 10/1987 | Köll | 502/230 |
| 5,102,851 | 4/1992 | Eri et al. | 502/302 |

FOREIGN PATENT DOCUMENTS

| | | |
|---|---|---|
| 2346943 | 9/1973 | Germany. |
| 01/287079 | 4/1989 | Japan. |

*Primary Examiner*—Bernard Dentz
*Attorney, Agent, or Firm*—Keil & Weinkauf

[57] ABSTRACT

A process for the preparation of unsaturated cyclic ethers of the general formula I

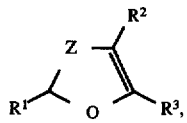
(I)

in which
Z denotes $-(CHR^4)_q-$ or $-(CHR^4)_q-O-$
q is 0, 1, 2 or 3 and
$R^1$, $R^2$, $R^3$, and $R^4$ denote hydrogen or $C_1-C_4$ alkyl from diols of the general formula II

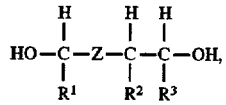
(II)

in which, $R^1$, $R^2$, and $R^3$ have the aforementioned meanings, in the presence of a cobalt-containing supported catalyst, wherein the cobalt-containing supported catalyst used contains cobalt and a noble metal—selected from the group consisting of platinum, palladium, rhodium, iridium, ruthenium, osmium, rhenium, or mixtures thereof—in an atomic ratio of from 0.5:1 to 70000:1 on an inert support and optionally basic alkali metal and alkaline earth metal salts, scandium, vanadium, chromium, manganese, iron, nickel, copper, zinc, germanium, tin, lead, antimony, bismuth, or mixtures thereof and the reaction is carried out in the liquid phase at temperatures ranging from 150° to 300° C., and also novel cobalt-containing supported catalysts, prepared, in particular, by sol impregnation.

5 Claims, No Drawings

PREPARATION OF UNSATURATED CYCLIC ETHERS

The present invention relates to a process for the preparation of unsaturated cyclic ethers from diols in the liquid phase over cobalt-containing supported catalysts and also to novel cobalt-containing supported catalysts, prepared, in particular, by sol impregnation.

DE-A 2,346,943 reveals a process for the preparation of unsaturated cyclic compounds from diols under a stream of hydrogen, in which the catalysts used are mixtures of a supported copper chromite catalyst or supported copper catalyst and a tungstic acid or heteropolytungstic acid. The conversions and yields are unsatisfactory.

JP 01/287079 reveals a process for the preparation of dihydrofurans and dihydropyrans from 1,4-butane diols and 1,5-pentane diols respectively over cobalt catalysts, which must be reduced with hydrogen at 600 dC.

U.S. Pat. No. 2,993,910 reveals a process for the preparation of dihydrofurans from 1,4-butane diols over cobalt catalysts, which must be reduced with hydrogen at from 300° to 450° C.

It is an object of the present invention to overcome the above drawbacks.

Accordingly we have found a novel and improved process for the preparation of unsaturated cyclic ethers of the general formula I

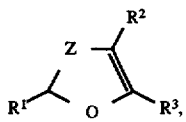

(I)

in which

Z denotes —(CHR$^4$)$_q$ or —(CHR$^4$)$_q$—O— q is 0, 1, 2 or 3 and

R$^1$, R$^2$, R$^3$, and R$^4$ denote hydrogen or C$_1$–C$_4$ alkyl from diols of the general formula II

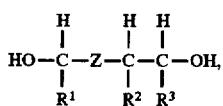

(II)

in which, R$^1$, R$^2$, and R$^3$ have the aforementioned meanings, in the presence of a cobalt-containing supported catalyst, wherein the cobalt-containing supported catalyst used contains cobalt and a noble metal—selected from the group consisting of platinum, palladium, rhodium, iridium, ruthenium, osmium, rhenium, or mixtures thereof—in an atomic ratio of from 0.5:1 to 70000:1 on an inert support and optionally basic alkali metal and alkaline earth metal salts, scandium, vanadium, chromium, manganese, iron, nickel, copper, zinc, germanium, tin, lead, antimony, bismuth, or mixtures thereof and the reaction is carried out in the liquid phase at temperatures ranging from 150° to 300° C., and also novel cobalt-containing supported catalysts, prepared, in particular, by sol impregnation.

The process of the invention can be carried out as follows:

The diol II can usually be caused to react using from 1 to 20 wt % and preferably from 2 to 10 wt % of cobalt-containing supported catalyst at temperatures ranging from 150° to 300° C. and preferably from 160° to 240° C. and the mixture formed can be distilled off from the unsaturated cyclic ether I and the water of reaction batchwise or, preferably, continuously. Optionally the unsaturated cyclic ether formed during the reaction may be stripped with gases inert under the reaction conditions, such as nitrogen or argon. In the continuous mode of operation the level of the liquid in the reaction vessel can be maintained by the addition of fresh diol II. In order to lower the content of saturated cyclic ethers that cannot be easily separated from the unsaturated cyclic ether, from 0.05 to 1 wt % and preferably from 0.1 to 0.3 wt % of alkali metal compounds and/or alkaline earth metal compounds may be metered to the reactor, eg in the form of hydroxide or carbonate.

Suitable cobalt-containing supported catalysts are the oxides of cobalt or metallic cobalt on a porous support and contain one or more noble metal elements selected from the group consisting of platinum, palladium, rhodium, iridium, ruthenium, osmium, rhenium, or mixtures thereof, preferably platinum, palladium, rhenium, or mixtures thereof, and more preferably platinum, palladium, or mixtures thereof, and optionally from 0.01 to 10 wt %, preferably from 0.1 to 5 wt % and more preferably from 0.5 to 3 wt % of basic alkali metal salts or alkaline earth metal salts, scandium, vanadium, chromium, manganese, iron, nickel, copper, zinc, germanium, tin, lead, antimony, bismuth, or mixture thereof (compound A), preferably lithium, potassium, sodium, calcium, strontium, barium, manganese, iron, nickel, copper, zinc, tin, antimony, or mixtures thereof, and more preferably potassium, sodium, manganese, iron, nickel, copper, zinc, or mixtures thereof.

The weight of cobalt or cobalt oxide in the supported catalyst is usually between 1 and 70 wt %, preferably between 5 and 50 wt % and more preferably between 10 and 40 wt %.

One or more elements selected from the group consisting of platinum, palladium, rhodium, iridium, ruthenium, osmium, rhenium, or mixtures thereof, preferably platinum, palladium, rhenium, or mixtures thereof, and more preferably platinum, palladium, or mixtures thereof, may be added to the catalyst to increase its activity.

The weight of these elements is between 0.001 and 2 wt %, preferably between 0.005 and 1 wt % and more preferably between 0.01 and 0.5 wt %.

The supported catalysts usually have a ratio by weight of cobalt to the noble metal of from 0.5:1 to 70,000:1, preferably from 5:1 to 10,000:1 and more preferably from 20:1 to 4,000:1.

Suitable supports are inert supports such as SiO$_2$, Al$_2$O$_3$, TiO$_2$, ZrO$_2$, zeolites of all types such as zeolites of fine porosity, eg A-type zeolite, zeolites of medium porosity, eg ZSM-5, ZSM-11, ferrierite, zeolites of coarse porosity, eg faujasites, β-zeolites, mordenite, offretite, hydrothermally prepared phosphates such as AlPO and SAPO, activated charcoals, or alkaline-earth oxides, preferably SiO$_2$, ZrO$_2$, and zeolites and more preferably SiO$_2$.

The supported catalysts usually have a surface area (BET) of from 1 to 600 m$^2$/g, preferably from 10 to 500 m$^2$/g and more preferably from 50 to 400 m$^2$/g.

The porosity of the supported catalysts is usually from 0.01 to 1.5 mL/g, preferably from 0.1 to 1.2 mL/g and more preferably from 0.2 to 1 mL/g.

The preparation of the supported catalysts is known in the art. An advantageous method is the impregnation of the porous support material with a soluble cobalt compound (eg a nitrite, nitrate, sulfite, sulfate, carbonate, hydroxide, or, inter alia carboxylates, halides, halites, halates), optionally simultaneously or successively with a likewise soluble compound A (eg as nitrite, nitrate, sulfite, sulfate, carbonate, hydroxide, carboxylates, halides, halites, halates), followed by thermal decomposition of the anion to form the oxide.

Another possibility comprises mixing a cobalt compound with the support material (dry or in suspension or, in particular, by spray drying), optionally simultaneously with a chemical compound A, compression of the material (eg by kneading, optionally with the addition of a suitable shaping agent), shaping by extrusion and drying, followed by calcination at temperatures ranging from 200° to 1300° C., preferably from 300° to 1000° C. and more preferably from 400° to 800° C.

The element A can alternatively be subsequently applied by impregnation, by spraying, or by using some other technique.

One or more of the noble metal components can be applied by impregnation with a soluble compound (nitrite, nitrate, sulfite, sulfate, phosphite, phosphate, carbonate, hydroxide, or, inter alia, carboxylates, halides, halites, halates) or as acids. Particularly preferred is the application of one or more of these metals in the form of a sol.

The substituents $R^1$, $R^2$, $R^3$, $R^4$, the connecting member Z, and the index q in the compounds I and II have the following meanings:

$R^1$, $R^2$, $R^3$, and $R^4$ independently denote hydrogen, $C_1$-$C_4$ alkyl such as methyl, ethyl, n-propyl, isopropyl, n-butyl, isobutyl, sec-butyl, and tert-butyl, preferably $C_1$-$C_3$ alkyl such as methyl, ethyl, n-propyl, and isopropyl and more preferably methyl and ethyl, Z denotes —$(CHR^4)_q$— or —$(CHR^4)_q$—O—, q is 0, 1, 2 or 3, preferably 0 or 1, more preferably 1.

powder (water uptake 1.85 mL/g) for approximately 2 h, dried over a period of 16 h at 120° C. and calcined over a period of 2 h at 500° C.

This composition (weight given in Table 1) was sprayed with a noble metal sol (0.6 g per liter) over a period of 2 h and then dried and calcined for 1 h at 500° C., which sol had been prepared by mixing a noble metal salt in 700 mL of water with 5 g of poly(vinyl pyrrolidone) and 300 mL of ethanol and refluxing over a period of 4 h.

Further details on the preparation and the properties of the catalysts are listed in Table 1:

TABLE 1

| Catalyst | Noble Metal Salt [g] | Weight of Co-containing $SiO_2$ [g] | Weight of Noble Metal Sol [mL] | Content of Noble Metal [wt %] | Surface Area BET [m²/g] |
|---|---|---|---|---|---|
| A | 1.46 $Pt(NO_3)_2$ | 310 | 260 | 0.05 | 219 |
| B | 1.46 $Pt(NO_3)_2$ | 328.6 | 548 | 0.1 | 215 |
| C | 1.3 $Pt(NO_3)_2$ | 332 | 277 | 0.05 | 221 |
| D | 2.92 $Ru(NO)(NO_3)_3$ | 332 | 277 | 0.05 | 241 |
| E | 1.172 $ReCl_5$ | 335 | 280 | 0.05 | 194 |

Preparation the catalysts F to H 555 mL of a solution of 291.3 g of $Co(NO_3)_2.6H_2O$ and a metal nitrate in water were stirred with 300 g of $SiO_2$ powder (water uptake 1.85 mL/g) for approximately 2 h, dried over a period of 16 h at 120° C. and calcined over a period of 2 h at 500° C.

This composition (weight given in Table 2) was placed on a rotary table and sprayed with 275 mL of a noble metal sol (0.6 g per liter) over a period of 2 h and then dried and calcined for 1 h at 500° C., which sol had been prepared by mixing a noble metal salt in 700 mL of water with 5 g of poly(vinyl pyrrolidone) and 300 mL of ethanol and refluxing over a period of 4 h.

Further details on the preparation and the properties of the catalysts are given in Table 2:

TABLE 2

| Cat. | Metal Nitrate [g] | Noble Metal Salt [g] | Weight of Co-containing $SiO_2$ [g] | Weight of Noble Metal Sol [mL] | Content of Noble Metal [wt %] | Surface Area BET [m²/g] |
|---|---|---|---|---|---|---|
| F | 0.98 $NaNO_3$ | 1.46 $Pt(NO_3)_2$ | 330.1 | 275 | 0.05 | 231 |
| G | 1.11 $KNO_3$ | 1.46 $Pt(NO_3)_2$ | 340.5 | 284 | 0.05 | 198 |
| H | 11.4 $Cu(NO_3)_2.3H_2O$ | 1.46 $Pt(NO_3)_2$ | 308 | 257 | 0.05 | 350 |

Examples of suitable diols II are 1,4-butane diol, 1,5-pentane diol, 1,6-hexane diol, or diethylene glycol.

Examples of suitable unsaturated cyclic ethers I are 3,4-dihydro-2H-pyran, 2,3-dihydrofuran, and 1,4-dioxane, preferably 3,4-dihydro-2H-pyran.

The unsaturated cyclic ethers I are valuable protective groups for alcohols.

EXAMPLES

Preparation of the catalysts A to E 555 mL of a solution of 291.3 g of $Co(NO_3)_2.6H_2O$ and a metal nitrate in water were stirred with 300 g of $SiO_2$ Preparation of catalyst J 555 mL of a solution of 291.3 g of $Co(NO_3)_2.6H_2O$ and a metal nitrate in water were stirred with 300 g of $SiO_2$ powder (water uptake 1.85 mL/g) for approximately 2 h, dried over a period of 16 h at 120° C. and calcined over a period of 2 h at 500° C.

336.4 g of the previously prepared composition were sprayed, on a rotary table over a period of 2 h, with 250 mL of an aqueous solution containing 0.41 g of $Pt(NO_3)_2$, and were then dried and calcined over a period of 1 h at 500° C. The resulting catalyst J contained 0.05 wt % of platinum and had a surface area (BET) of 211 m²/g.

Comparative catalyst X (as described in U.S. Pat. No. 2,993,910)

740 mL of a solution of 388.4 g of Co(NO₃)₂.6H₂O in water were stirred with 400 g of SiO₂ powder (water uptake 1.85 mL/g) over a period of approximately 2 h, dried over a period of t 6 h at 120° C. and calcined over a period of 2 h at 500° C. (surface area (BET): 230 m²/g).

1.4 liters of 1,5-pentane diol and the an amount of a catalyst A to J (as given in Table 3) were placed in a vessel and heated with stirring to the lower limit of the temperature range heated and the 3,4-dihydro-2H-pyran/water mixture formed was continuously removed by distillation. A total amount of 1,5-pentane diol (given in Table 3) was metered in continuously over the period of time stated in Table 3. Following phase separation of the distillate 3,4-dihydro-2H-pyran was obtained in an amount and with specifications as given in Table 3.

TABLE 3

| Ex. No. | Cat. [g] | Temp. [°C.] | Time [h] | Total Weight of 1,5-Pentane-diol [g] | Yield of 3,4-Dihydro-2H-pyran [g/%] | Purity [wt %] | Content of Tetrahydropyran [wt %] |
|---|---|---|---|---|---|---|---|
| 1 | 45 A | 180–215 | 200 | 10,950 | 8498/98 | 97 | 1.5 |
| 2 | 45 B | 180–215 | 200 | 11,112 | 8639/98 | 96 | 1.3 |
| 3* | 30 C | 190–235 | 100 | 5,562 | 4144/94 | 95 | 1.3 |
| 4 | 30 D | 190–235 | 50 | 2,240 | 1715/97 | 96 | 2 |
| 5 | 45 E | 180–230 | 100 | 5,500 | 4300/99 | 98 | 1 |
| 6 | 45 F | 185–225 | 200 | 11,109 | 8613/98 | 95 | 1.8 |
| 7 | 45 G | 185–235 | 200 | 10,830 | 8361/98 | 96 | 1.3 |
| 8 | 45 H | 160–215 | 200 | 10,008 | 7671/97 | 95 | 1.4 |
| 9 | 45 J | 180–215 | 200 | 10,946 | 8513/98 | 96 | 1.6 |
| V1** | 45 J | 185–240 | 200 | 8,090 | 5897/92 | 91 | 6.7 |

*addition of 10 mL of a 1% strength aqueous potassium carbonate solution
**comparative example (as described in US-A 2,993,910)

We claim:

1. A process for the preparation of an unsaturated cyclic ether of the formula I

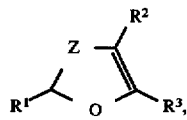

(I)

in which

Z denotes —(CHR⁴)$_q$ or —(CHR⁴)$_q$—O—
q is 0, 1, 2 or 3 and
R¹, R², R³ and R⁴ denote hydrogen or C₁–C₄-alkyl from diols of the formula II

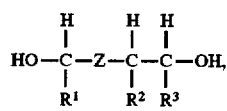

(II)

in which R¹, R², and R³ have the aforementioned meanings, in the presence of a cobalt-containing supported catalyst, wherein the cobalt-containing supported catalyst used is not reduced prior to the commencement of the reaction and contains cobalt and a noble metal—selected from the group consisting of platinum, palladium, rhodium, iridium, ruthenium, osmium, rhenium, or mixtures thereof—in an atomic ratio of from 0.5:1 to 70000:1 on an inert support, wherein the noble metal is applied in the form of a sol to the cobalt containing supported catalyst, and optionally basic alkali metal and alkaline earth metal salts, scandium, vanadium, chromium, manganese, iron, nickel, copper, zinc, germanium, tin, lead, antimony, bismuth, or mixtures thereof and the reaction is carried out in the liquid phase at temperatures ranging from 150° to 300° C.

2. A process for the preparation of an unsaturated cyclic ether I as defined in claim 1, wherein the cobalt-containing supported catalyst used contains from 1 to 70 wt % of cobalt and from 0.001 to 2 wt % of one or more noble metals.

3. A process for the preparation of an unsaturated cyclic ether I as defined in claim 1, wherein the cobalt-containing supported catalyst used contains from 0.001 to 10 wt % of basic alkali metal salts or alkaline earth metal salts or mixtures thereof, based on the total metal present.

4. A process for the preparation of an unsaturated cyclic ether I as defined in claim 1, wherein from 0.05 to 1 wt % of basic alkali metal salts or alkaline earth metal salts or mixtures thereof, based on I, is added during the reaction.

5. A process for the preparation of an unsaturated cyclic ether I as defined in claim 1, wherein the cobalt-containing supported catalyst used contains from 0.01 to 10 wt % of scandium, vanadium, chromium, manganese, iron, nickel, copper, zinc, germanium, tin, lead, antimony, bismuth, or mixtures thereof, based on the total metal present.

* * * * *